(12) United States Patent
Poechlauer et al.

(10) Patent No.: US 7,052,885 B2
(45) Date of Patent: May 30, 2006

(54) PROCESS FOR PREPARING HETEROCYCLIC (R)- AND (S)-CYANOHYDRINS

(75) Inventors: Peter Poechlauer, Linz (AT); Wolfgang Skranc, Vienna (AT); Herbert Mayrhofer, Engerwitzdorf (AT); Irma Wirth, Enns (AT); Rudolf Neuhofer, Mittertreffling (AT); Herfried Griengl, Graz (AT); Martin Fechter, Graz (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 331 days.

(21) Appl. No.: 10/325,922

(22) Filed: Dec. 23, 2002

(65) Prior Publication Data
US 2003/0129712 A1    Jul. 10, 2003

(30) Foreign Application Priority Data
Dec. 27, 2001    (AT)    .............................. A 2033/2001

(51) Int. Cl.
C12P 17/00    (2006.01)
C12P 17/02    (2006.01)
C12P 17/04    (2006.01)
C12P 17/06    (2006.01)
C12P 17/18    (2006.01)

(52) U.S. Cl. ...................... 435/117; 435/118; 435/119; 435/120; 435/121; 435/122; 435/123; 435/124; 435/125; 435/126; 435/232

(58) Field of Classification Search ................ 435/117, 435/118, 121, 120, 122, 123, 124, 125, 126, 435/232, 12
See application file for complete search history.

(56) References Cited

U.S. PATENT DOCUMENTS

| 5,008,192 | A | 4/1991 | Neidermeyer et al. |
| 5,714,356 | A | 2/1998 | Griengl et al. |
| 6,225,095 | B1 | 5/2001 | Pochlauer et al. |
| 6,337,196 | B1 | 1/2002 | Kirchner et al. |
| 2002/0006646 | A1 * | 1/2002 | Semba et al. ............... 435/136 |

FOREIGN PATENT DOCUMENTS

AT    408 231    2/2001

* cited by examiner

Primary Examiner—Herbert J. Lilling
(74) Attorney, Agent, or Firm—Wenderoth, Lind & Ponack, L.L.P.

(57) ABSTRACT

A process for preparing enantiomer-enriched heterocyclic (R)- and (S)-cyanohydrins of the formula (I),

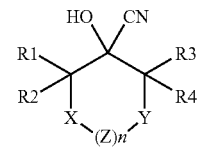

where R1, R2, R3, R4 independently of one another are H, an unsubstituted or substituted $C_1$–$C_{24}$-alkyl, alkenyl or alkynyl radical, where one or more carbon atoms in the chain can be replaced by an oxygen atom, a nitrogen atom, a sulfur atom, an SO or an $SO_2$ group, an unsubstituted or substituted aryl or heteroaryl radical or heterocyclic radical or halogen, hydroxyl, NR5R6, acetyl, oxo, $C_1$–$C_6$-carbalkoxy, $C_1$–$C_6$-carbalkoxyamino, COOR7, cyano, amide, benzoylamino or $NO_2$, R5 and R6 are H, $C_1$–$C_6$-alkyl radical, phenyl radical, benzyl radical or COOR7, or together form a $C_2$–$C_8$-alkylene or heteroalkylene radical, R7 is H or $C_1$–$C_6$-alkyl, n is 0, 1, 2 or 3, X, Y and Z can be an unsubstituted or substituted carbon atom or a radical selected from the group consisting of N, O, S or NR5R6, where R5 and R6 are as defined above, SO or $SO_2$, and at least one of the radicals X, Y and Z is not a carbon atom, where the compounds of the formula (I) can have one or more double bonds in the ring, with the proviso that in a 5-membered ring the double bond is not conjugated with the —C(OH)CN-group, and/or can be anellated and/or bridged, by reacting a ketone of the formula (II),

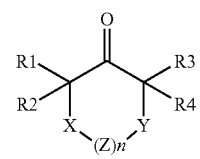

where R1, R2, R3, R4, X, Y, Z and n have the meanings above, with an (R)- or (S)-hydroxynitrile lyase in an organic, aqueous or two-phase system, or in emulsion, in the presence of a cyanide group donor.

8 Claims, No Drawings

PROCESS FOR PREPARING HETEROCYCLIC (R)- AND (S)-CYANOHYDRINS

The invention relates to an enzyme-catalyzed process for preparing enantiomer-enriched heterocyclic (R)- and (S)-cyanohydrins using (R)- or (S)-hydroxynitrile lyase (HNL) from the corresponding heterocyclic ketones, and their further reaction to form the corresponding acids, esters or amides.

Cyanohydrins are of importance for the synthesis of alpha-hydroxyacids, alpha-hydroxyketones, beta-aminoalcohols, which are used to produce biologically active substances, for example active pharmaceutical compounds, vitamins, or else pyrethroid compounds.

These cyanohydrins are prepared by adding prussic acid to the carbonyl group of a ketone or aldehyde.

The literature already discloses a plurality of process variants which describe the preparation of (R)- and/or (S)-cyanohydrins from aliphatic, aromatic or heteroaromatic aldehydes or else from aliphatic or aromatic ketones.

Thus EP-A-0 326 063 discloses an enzymatic process for preparing optically active (R)- or (S)-cyanohydrins by reacting aliphatic, aromatic or heteroaromatic aldehydes or ketones with prussic acid in the presence of (R)-oxynitrilase (EC 4.1.2.10) from *Prunus amygdalus* or oxynitrilase (EC 4.1.2.11) from Sorghum bicolor, but examples of ketones, in particular heterocyclic ketones, are not described.

EP 0 632 130 further describes a process in which aliphatic aldehydes or unsymmetrical aliphatic ketones are reacted with prussic acid and oxynitrilase from *Hevea brasiliensis* in a stereospecific manner to give (S)-cyanohydrins. Heterocyclic ketones are not mentioned.

EP 0 927 766 describes an enzymatic process for preparing optically active (S)-cyanohydrins from aliphatic, aromatic or heteroaromatic aldehydes or ketones in emulsion. The only heteroaromatic ketone cited here is indolylacetone. Ketones whose keto group is part of the heterocycle are not encompassed by EP 0 927 766.

Cyanohydrins from heterocyclic ketones whose keto group is a constituent of the heterocycle, for instance 7-oxabicyclo[2.2.1]hept-2-ene derivatives, have previously been prepared, for example, by $ZnI_2$-catalyzed Diels-Alder addition of furan and acetoxyacylnitrile, as described in Helv. Chim. Acta (1984), 67(6), 1612–1615. Optically active cyanohydrins have been obtained in this process using racemate separation via a cyanohydrin-brucin-complex. A further potential method is the preparation of cyanofuranones, for example from $MeCH(OH)CO_2Et$ and crotononitrile in THF and in the presence of NaH, as disclosed by U.S. Pat. No. 4,208,338.

It was an object of the invention to find a process which makes possible the preparation of enantiomer-enriched heterocyclic (R)- and (S)-cyanohydrins from the corresponding heterocyclic ketones in a simple manner, in high yields and with high enantiomeric purity.

Unexpectedly, this object was achieved by the (R)- or (S)-HNL-catalyzed reaction of heterocyclic ketones.

The present invention therefore relates to a process for preparing enantiomer-enriched heterocyclic (R)- und (S)-cyanohydrins of the formula (I),

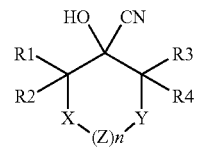

where R1, R2, R3, R4 independently of one another are H, an unbranched, branched or cyclic $C_1$–$C_{24}$-alkyl, alkenyl or alkynyl radical which can be unsubstituted, monosubstituted or polysubstituted by substituents inert under the reaction conditions, where one or more carbon atoms in the chain can be replaced by an oxygen atom, a nitrogen atom, a sulfur atom, an SO or an $SO_2$ group, an aryl or heteroaryl or heterocyclic radical which can be unsubstituted, monosubstituted or polysubstituted by substituents inert under the reaction conditions, or halogen, hydroxyl, NR5R6, acetyl, oxo, $C_1$–$C_6$-carbalkoxy, $C_1$–$C_6$-carbalkoxyamino, COOR7, cyano, amide, benzoylamino or $NO_2$, R5 and R6 independently of one another can be H, unbranched, branched or cyclic $C_1$–$C_6$-alkyl radical, phenyl radical, benzyl radical, COOR7, or together form a $C_2$–$C_8$-alkylene or -heteroalkylene radical, R7 is H or $C_1$–$C_6$-alkyl, X and Y independently of one another can be a carbon atom which can be unsubstituted, monosubstituted or disubstituted by substituents inert under the reaction conditions, or a radical selected from the group consisting of N, O, S, or NR5R6, where R5 and R6 are as defined above, SO or $SO_2$, n is 0, 1, 2 or 3, Z is a carbon atom which can be unsubstituted, monosubstituted or disubstituted by substituents inert under the reaction conditions, or a radical selected from the group consisting of N, O, S, or NR5R6, where R5 and R6 are as defined above, SO or $SO_2$, and at least one of the radicals X, Y and Z is not a carbon atom, where the compounds of the formula (I), depending on the ring size, can have one or more double bonds in the ring, with the proviso that in the 5-membered ring the double bond is not conjugated with the —C(OH)CN-group, and/or can be monoanellated or polyanellated by 5-membered, 6-membered or 7-membered rings containing 0 to 3 heteroatoms, and/or can be bridged by an unbranched or branched $C_1$–$C_6$-alkylene radical, the alkyl chain of which can be interrupted by one or more heteroatoms and/or can have a double bond, which comprises reacting ketones of the formula (II),

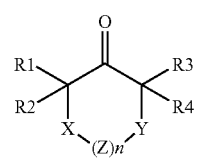

where R1, R2, R3, R4, X, Y, Z and n have the meanings given above, using an (R)- or (S)-hydroxynitrile lyase in the organic, aqueous or two-phase system or in emulsion in the presence of a cyanide-group donor to give the desired (R)- or (S)-cyanohydrins.

In the formula (I) and in formula (II), R1, R2, R3, R4 independently of one another are H or can be an unbranched, branched or cyclic $C_1$–$C_{24}$-alkyl, alkenyl or alkynyl radical which can be unsubstituted or monosubstituted or polysubstituted by substituents inert under the reaction conditions.

Alkyl, Alkenyl or Alkynyl are taken to mean here saturated or mono- or polyunsaturated unbranched, branched or cyclic, primary, secondary or tertiary hydrocarbon radicals. These are $C_1$–$C_{24}$-alkyl, alkenyl or alkynyl radicals, for instance methyl, ethyl, vinyl, ethynyl, propyl, isopropyl, allyl, propenyl, 1-methylcyclopropenyl, butyl, isobutyl, t-butyl, 1,3-butadienyl, 2-methyl-1,3-butadienyl, pentyl, cyclopentyl, isopentyl, neo-pentyl, 2-pentynyl, 1,3-pentadiynyl, hexyl, isohexyl, 1,2-hexadienyl, cyclohexyl, cyclohexylmethyl, 3-methylpentyl, 2,2-dimethylbutyl, 2,3-dimethylbutyl, octyl, isooctyl, cyclooctyl, 2,6-dimethyloctane, decyl, cyclodecyl, dodecyl, cyclododecyl, 2,6,10-trimethyldodecanyl, etc.

Preference is given here to $C_1$–$C_{12}$-alkyl radicals and $C_2$–$C_{12}$-alkenyl or alkynyl radicals, and particular preference is given to $C_2$–$C_8$-alkyl, alkenyl or alkynyl radicals. In these radicals, one or more carbon atoms in the chain can be replaced by an oxygen atom, a nitrogen atom, a sulfur atom or an SO or $SO_2$ group, so that ethers, amides, amines, imines, thioethers, sulfoxides and sulfonyls are obtained.

Examples of these are 2-methoxypropyl, 2-methoxybutyl, oxiranyl, tetrahydrofuryl, dioxanyl, 2-ethoxymethyl, 2-propoxymethyl, N',N'-dimethylhydrazino, ethylthiomethyl, 1,1-dioxotetrahydrothiophenyl, methylsulfinylmethyl, methylsulfonylmethyl, thiiranyl etc.

Suitable substituents which are inert under the reaction conditions are, for example, the following groups:

$C_1$–$C_{20}$-alkoxy or alkylalkoxy or aryloxy groups, for instance methoxy, ethoxy, butoxy, hexoxy, methoxymethyl, methoxyethyl, ethoxymethyl, ethoxyethyl, phenyloxy, etc.; nitro, halogen, hydroxyl, oxo, CN, $CONH_2$, carboxyl, carboxylic esters or carboxamides, primary, secondary or tertiary amino groups, $SO_3H$ groups, phenyl which can be unsubstituted or monosubstituted or polysubstituted by halogen, hydroxyl, $C_1$–$C_4$-alkyl or alkoxy etc.

Preferred substituents are $C_1$–$C_6$-alkoxy, $C_1$–$C_{12}$-alkylalkoxy, $C_1$–$C_{20}$-aryloxy, halogen, hydroxyl, oxo, carboxyl, phenyl which can be unsubstituted or monosubstituted or disubstituted by halogen, hydroxyl, $C_1$–$C_4$-alkyl or $C_1$–$C_4$-alkoxy.

R1, R2, R3, R4 can, however, also be an aryl or heteroaryl radical or heterocyclic radical which can be unsubstituted or monosubstituted or polysubstituted by substituents inert under the reaction conditions.

Aryl is preferably taken to mean $C_6$–$C_{20}$-aryl groups, for instance phenyl, biphenyl, naphthyl, indenyl, fluorenyl etc.

The aryl group can be monosubstituted or polysubstituted by substituents listed above which are inert under the reaction conditions.

Heteroaryl or heterocycle is taken to mean cyclic radicals which contain at least one O, S or N atom in the ring. These are, for example, furyl, thiophenyl, pyridyl, pyrimidyl, imidazolyl, tetrazolyl, pyrazinyl, benzofuranyl, quinolyl, isoquinolyl, isobenzofuryl, pyrazolyl, indolyl, isoindolyl, benzoimidazolyl, purinyl, carbazolyl, oxazolyl, isoxazolyl, pyrrolyl, quinazolinyl, pyridazinyl, phthalazinyl, morpholinyl etc. Functional O or N groups can be protected here if necessary.

The heteroaryl groups or the heterocycle can be unsubstituted or monosubstituted or polysubstituted by the substituents already listed above.

In addition, R1, R2, R3, R4 can also be halogen, for instance fluorine or chlorine, boron, hydroxyl, NR5R6, acetyl, oxo, $C_1$–$C_6$-carbalkoxy, COOR7, cyano, $NO_2$, amide or benzoylamino.

R5 and R6 here are independently of one another H, an unbranched, branched or cyclic $C_1$–$C_6$-alkyl radical, phenyl radical, benzyl radical or COOR7 or together form a $C_2$–$C_8$-alkylene or $C_2$–$C_8$-heteroalkylene radical.

R7 is H or $C_1$–$C_6$-alkyl.

Preferably, R1, R2, R3 and R4 independently of one another are H, a saturated or monounsaturated, unbranched, branched or cyclic $C_1$–$C_{12}$-alkyl radical in which one carbon atom in the chain can be replaced by an oxygen atom, a nitrogen atom or a sulfur atom, a phenyl, biphenyl or naphthyl radical, or halogen, hydroxyl, oxo, $C_1$–$C_6$-carbalkoxy, $C_1$–$C_6$-carbalkoxyamino, NR5R6, acetyl, COOR7, cyano, amide, benzoylamino or $NO_2$, R5 and R6 independently of one another can be H or an unbranched, cyclic or branched $C_1$–$C_6$-alkyl radical or together form a $C_2$–$C_8$-alkylene radical, and R7 is H or $C_1$–$C_6$-alkyl.

n is 0, 1, 2 or 3, as a result of which 5-membered, 6-membered, 7-membered or 8-membered Rings are obtained. Preferably, n is 0, 1 or 2 and particularly preferably n is 0 or 1.

X, Y and Z independently of one another can be a carbon atom which can be unsubstituted or monosubstituted or disubstituted by substituents inert under the reaction conditions, or a radical selected from the group consisting of N, O, S, or NR5R6, where R5 and R6 are as defined above, SO or $SO_2$, where at least one of the radicals X, Y and Z is not a carbon atom. Preferably, only one or two of the radicals X, Y and Z, particularly preferably only one of the radicals X, Y and Z, is a radical selected from the group consisting of N, O, S, NR5R6, SO or $SO_2$.

Suitable substituents which are inert under the reaction conditions are again the substituents already listed above.

Preferably, X, Y and Z are a carbon atom which can be unsubstituted or monosubstituted or disubstituted by $C_1$–$C_6$-alkyl, $C_1$–$C_6$-alkoxy, $C_1$–$C_{12}$-alkylalkoxy, $C_1$–$C_{20}$-aryloxy, halogen, hydroxyl, oxo, carboxyl, phenyl which can be unsubstituted or monosubstituted or disubstituted by halogen, hydroxyl, $C_1$–$C_4$-alkyl or $C_1$–$C_4$-alkoxy, or a radical selected from the group consisting of N, O, S or NR5R6, where one or two of the radicals X, Y or Z is not a carbon atom.

The compounds of the formula (I) and of the formula (II) can, depending on the ring size, contain one or more double bonds in the ring, in which case, in the 5-membered ring, the double bond must not be conjugated with the —C(OH)CN-group.

Preferably, 5-membered rings do not contain a double bond in the ring. 6-membered rings preferably contain no double bond, or at most one double bond, in the ring, whereas in 7-membered and 8-membered rings, zero to two double bonds are preferred.

The compounds of the formula (I) and of the formula (II) can also, again depending on the ring size, be monoanellated or polyanellated by 5-membered, 6-membered or 7-membered rings containing 0 to 3, preferably 0 to 1, heteroatoms. Preferably, the compounds of the formula (I) are not anellated or are anellated by a 5-membered or 6-membered ring.

In addition, the compounds of the formula (I) and the formula (II) can be bridged by an unbranched or branched $C_1$–$C_6$-alkylene radical. The alkylene chain can in this case also contain a double bond and/or be interrupted by one or more heteroatoms.

Preferably, the chain is not interrupted by a heteroatom, or is interruped by at most one heteroatom.

In the inventive process, ketones of the formula (II), some of which are commercially available, or can be synthesized, for example in a similar manner to J. Org. Chem., 1970, 35, 898–902; or in accordance with the literature Synthesis, 1978, 368–370, are reacted to form enantiomer-enriched heterocyclic (R)- and (S)-cyanohydrins.

The corresponding ketones of the formula (II) are reacted here using an (R)- or (S)-hydroxynitrile lyase in the presence of a cyanide group donor.

Suitable cyanide group donors are prussic acid, alkali metal cyanides or cyanohydrins of the general formula (III)

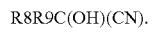

R8R9C(OH)(CN).

In the formula (III) R8 and R9 independently of one another are hydrogen or an unsubstituted hydrocarbon group, or R8 and R9 togtether are an alkylene group having 4 or 5 carbon atoms, where R8 and R9 are not simultaneously hydrogen. The hydrocarbon groups are aliphatic or aromatic, preferably aliphatic, groups. Preferably, R8 and R9 are alkyl groups having 1–6 carbon atoms, very preferably, acetocyanohydrin is a cyanide group donor of the formula (III).

The cyanide group donor can be prepared by known processes. Cyanohydrins, in particular acetocyanohydrin, are allso commercially available.

Preferably, prussic acid, KCN, NaCN, or acetocyanohydrin, particularly preferably prussic acid, is used as a cyanide group donor.

The prussic acid can also be liberated just before the reaction from one of its salts, for instance NaCN or KCN, and added without solvent or in dissolved form to the reaction mixture.

The cyanide group donor is used in a molar ratio to the compound of the formula (II) of 0.5:1 to 7:1, preferably from 0.8:1 to 6:1, and particularly preferably from 1:1 to 5:1.

The reaction can be carried out in an organic, aqueous or two-phase system or in emulsion.

Organic diluents which can be used are water-immiscible, or only slightly water-miscible, aliphatic or aromatic hydrocarbons, which may be halogenated, alcohols, ethers or esters or mixtures thereof. Preferably, t-butyl methyl ether, diisopropyl ether, dibutyl ether and ethyl acetat or mixtures thereof are used.

In the enantioselective reaction, the aqueous system used is an aqueous solution or buffer solution containing the appropriate HNL. Examples of these are acetate buffer, borate buffer, phthalate buffer, citrate buffer or phosphate buffer solution or mixtures thereof.

The HNLs can be present either as such or immobilized in the organic diluent, but the reaction can also be performed in a two-phase system or in emulsion using non-immobilized HNL.

Suitable HNLs are not only native, but also recombinant, (R)- and (S)-HNLs.

Suitable (S)-hydroxynitrile lyases which can be used are native (S)-hydroxynitrile lyases, for example from manioc and Hevea brasiliensis, and recombinant (S)-HNL. Preferably, the native HNL used is that from Hevea brasiliensis. Suitable recombinant (S)-HNLs are obtained, for example, from genetically modified microorganisms, for instance Pichia pastoris; E. coli or Saccharomyces cerevisiae.

Preferably, recombinant (S)-HNL from Pichia pastoris or E. coli are used.

Suitable (R)-HNLs are, for example, (R)-hydroxynitrile lyases from Prunus amygdalus, Prunus laurocerasus or Prunus serotina, or recombinant (R)-HNLs.

Preferably, (R)-hydroxynitrile lyase from Prunus amygdalus, or a recombinant (R)-HNL, is used.

Suitable (R)- and (S)-HNLs are disclosed, for example by WO 97/03204, EP 0 969 095; EP 0 951 561, EP 0 927 766, EP 0 632 130, EP 0547 655, EP 0 326 063, WO 01/44487 etc.

Per g of ketone, from about 0.1 to 20 g of diluent, and from 10 to 50000 IU, preferably from 1000 to 40000 IU, of activity of hydroxynitrile lyase are added.

The reaction mixture is shaken or stirred at temperatures from about −10° C. up to the deactivation temperature of the hydroxynitrile lyase, preferably at from −5 to +30° C., or if the reaction takes place in emulsion, is stirred at temperatures from 0° C. to about +30° C. so that an emulsion is formed.

To work up the reaction mixture, and to isolate the cyanohydrin formed, when the reaction is carried out in emulsion, customary techniques which first break the emulsion, for instance filtration, centrifugation or coalescence, are used. The phases which form are then separated, possibly with addition of demulsifiers, and the product-containing phase is worked up.

To produce the corresponding cyanohydrin, depending on the end product, known techniques such as distillation, extraction or crystallization are employed. Te cyanohydrins thus produced can, if appropriate, be stabilized by adding an acid before further processing.

In the case of extraction, organic solvents which are water-immiscible are used, for instance aliphatic or aromatic non-halogenated or halogenated hydrocarbons, for example, pentane, hexane, benzene, toluene, methylene chloride, chloroform, chlorobenzenes, ethers, for instance t-butyl methyl ether, diethyl ether, diisopropyl ether or esters, for example ethyl acetate or mixtures of such solvents are used.

If the purity of the extracted product should not be sufficient, a purification operation can follow. The purification can be performed by a known method and is best performed successfully by chromatography.

The inventively prepared (R)- or (S)-cyanohydrins of the formula (I) are obtained in high yields and having a high optical purity.

The cyanohydrins of the formula (I), if desired, can be further processed, as a result of which the corresponding hydroxy carboxylic acids, esters thereof and corresponding ethers or amides can be obtained.

The corresponding (R)- and (S)-cyanohydrin of the formula (I) can be hydrolyzed with concentrated sulfuric acid, without further purification, in a similar manner to the prior art, for example, as described in Angew. Chem. 1994, 106, 1615 or in Tetrahedron Letters 1990, Vol. 31, No. 9, 1249–1252, for example after extraction or if appropriate after filtering off the enzyme and distilling off the solvent. For the hydrolysis, other suitable acids, for instance $H_2SO_4$, can also be used, but preferably HCl is used.

The resultant (R)- and (S)-α-hydroxycarboxylic acids can then be purified, if appropriate, by recrystallization, for instance as described in EP 1 148 042.

The (R)- and (S)-α-hydroxycarboxylic acids can in turn be converted into the corresponding ether by reaction with an alkyl iodide compound, for exampe with methyl iodide, in the presence of Ag salts, as described, for instance, in Bull. Chem. Soc. Jpn., 1967, 40, 373–378.

Corresponding amides can be prepared from cyanohydrins of the formula (I), for example by partial hydrolysis with HBF$_4$ in CH$_2$Cl$_2$ at 0° C., as described, for instance in Tetrahedron Asymmetry, 1997, 8, 3503–3511.

Corresponding esters are prepared, for example, by acylation with acetyl chloride and pyridin in CH$_2$Cl$_2$, as described, for instance, in Tetrahedron, 1998, 54, 14477–14486.

The invention therefore further relates to the use of the inventively prepared (R)- or (S)-cyanohydrins of the formula (I) for preparing the corresponding hydroxycarboxylic acids, ethers, esters and amides.

EXAMPLE 1

Synthesis of (S)-3-cyanotetrahydrothiophen-3-ol

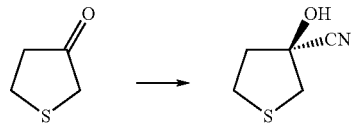

10.2 g (0.1 mol) of 4,5-dihydro-3(2H)-thiophenone were dissolved in 35 mL of t-butyl methyl ether and cooled to 0° C.

31 mL of (S)-HNL from *Hevea brasiliensis* havig an activity of 6500 IU/mL were mixed with 24 mL of a 50 mmol K$_2$HPO$_4$/citrate buffer of pH 4.00 and adjusted to pH 4.50 using 10% citric acid. This aqueous enzymatic solution was added to the organic solution and stirred for 5 minutes at 0° C. to form an emulsion. 13.5 g (0.5 mol) of HCN were then added to the reaction solution within 40 minutes with intensive stirring. After 75 minutes, 100 mL of t-butyl methyl ether were added dropwise to the reaction and the mixture was stirred for a further 30 minutes.

After phase separation had been completed, the aqueous phase was again extracted with 100 mL of t-butyl methyl ether and the combined organic phases were dried over Na$_2$SO$_4$, filtered and freed from the solvent.

Yield: 10.26 g of yellow oil (79.4% yield, 91.3% ee)

EXAMPLE 2

Synthesis of (S)-3-hydroxytetrahydrothiophene-3-carboxylic Acid

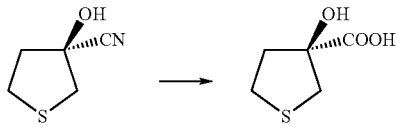

6.0 g (0.046 mol) of (S)-3-cyanotetrahydrothiophene-3-ol, prepared as in Example 1, were suspended in 15.4 mL concentrated HCl and heated to 70° C. After stirring for 15 hours at 70° C., the solution was cooled, made basic, using aqueous NaOH and extracted twice with t-butyl methyl ether. The yellow acqueous phase was adjusted to pH 1 with HCl and extracted twice with t-butyl methyl ether. The combined t-butyl methyl ether phases were washed with NaCl solution, dried over Na$_2$SO$_4$, filtered and freed from the solvent.

Yield: 3.85 g of beige solid (55.9% yield, 91.3% ee)

To determine the chirality of the acid, the salt with (S)-phenylethylamine was prepared and the absolute configuration of the acid was determined via its x-ray structure.

EXAMPLE 3

Synthesis of (S)-3-cyanotetrahydrofuran-3-ol

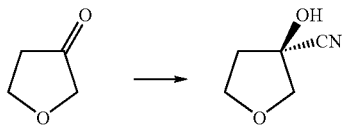

0.52 g (6.05 mmol) of 4,5-dihydro-3(2H)-furanone were dissolved in 3.5 mL of t-butyl methyl ether and cooled to 0° C.

3.10 mL of (R)-HNL from *Prunus amygdalus* having an activity of 2100 IU/mL were mixed with 2.4 mL of a 50 mmol K$_2$HPO$_4$/citrate buffer of pH 4.00 and adjusted to pH 4.50 with 10% citric acid. This aqueous phase was added to the orgaic phase and stirred for 5 minutes at 0° C. Then 0.76 g (28 mmol) of HCN were added all at once and stirred for 1 h. The reaction solution was extracted three times with t-butyl methyl ether and the combined organic phases were freed from solvent.

Yield: 92% conversion with 24% ee, light yellow oil

EXYMPLE 4

Synthesis of (S)-3-cyanotetrahydropyran-3-ol

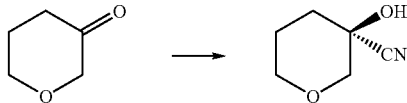

0.200 g (2 mmol) of tetrahydro-4H-pyran-3-one were dissolved in 3 mL of t-butyl methyl ether and cooled to 0° C.

0.3 mL of (S)-HNL from *Hevea brasiliensis* having an activity of 5100 IU/mL were mixed with 3 mL of distilled water and adjusted to pH 4.70 with 10% citric acid. This aqueous enzymatic solution was added to the organic solution and stirred for 15 minuten at 0° C. to form an emulsion. 0.3 mL (8.8 mmol) of HCN were then added to the reaction solution. After stirring for 60 minutes at 0° C., 3 mL of t-butyl methyl ether were added to the reaction and bound with 0.5 g of Celite® 545 water and enzyme. The mixture was then dried over Na$_2$SO$_4$, filtered and freed from solvent.

Yield: (98% Conversion) colorless oil of (S)-3-cyanotetrahydropyran-3-ol of 44% ee For analytical purposes, the cyanohydrin was converted into the corresponding acetate and characterized as such.

44% ee; $^1$H NMR: δ (ppm) 4.05 (d, J=12.1 Hz, 1H; H-2), 3.51 (d, 1H; H-2'), 3.87–3.61 (m, 2H; H-6, H-6'), 2.38 (m, 1H; H-4), 2.15 (m, 1H; H4'), 2.13 (s, 3H; Ac—CH$_3$), 1.85 (m, 2H; H-5, H-5'); $^{13}$C NMR: δ (ppm), 168.99 (Ac-C=O), 117.39 (CN), 68.93, 68.09 (C-2, C-6), 32.83, 30.52 (C-4, C-5), 22.03 (Ac—CH$_3$).

EXAMPLE 5

Reaction of rac-2-methyltetrahydrofuran-3-one

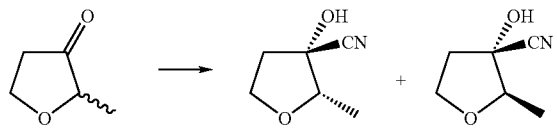

0.200 g (2 mmol) of 2-methyltetrahydrofuran-3-one were dissolved in 3 mL of t-butyl methyl ether and cooled to 0° C.

1.5 mL of (S)-HNL from *Hevea brasiliensis* having an activity of 5100 IU/mL were diluted with 1.5 mL of distilled water and adjusted to pH 5.20 with 10% citric acid. This aqueous enzymatic solution was added to the organic solution and stirred for 15 minutes at 0° C. to form an emusion. 0.3 mL (8.8 mmol) HCN were then added to the reaction solution. After stirring for 60 minutes at 0° C., 3 mL of t-butyl methyl ether were added to the reaction and bound with 0.5 g Celite® 545 water and enzyme. Then the mixture was dried over $Na_2SO_4$, filtered and freed from solvent.

Yield: (99% conversion) colorless oil of 3-cyano-2-methyltetrahydrofuran-3-ol

For analytical purposes, the cyanohydrin was converted into the corresponding acetate and characterized as such.

(+)-cis Isomer: 27% de; $^1$H NMR: δ (ppm) 4.13-4.04 (m, 1H; H-5), 4.04 (qu, J=6.3 Hz, 1H; H-2), 3.85 (ddd, J=18.0, 8.8, 6.9 Hz 1H; H-5'), 2.71 (ddd, J=14.0, 8.8, 8.2 Hz 1H; H-4),2.43 (ddd, J=14.0, 6.9, 3.5 Hz 1H; H4'), 2.15 (s, 3H; Ac—$CH_3$), 1.50 (d, J=6.3 Hz, 3H; $CH_3$); $^{13}$C NMR: δ (ppm), 169.23 (Ac—C=O), 116.35 (CN), 81.98 (C-5), 78.78 (C-3), 65.87 (C-2), 38.86 (C-4), 20.79 (Ac—$CH_3$), 17.32 ($CH_3$).

(+)-trans Isomer: 50% de; $^1$H NMR: δ (ppm) 4.13–4.02 (m, 1H; H-5), 4.11 (qu, J=6.3 Hz, 1H; H-2), 3.88 (ddd, J=17.6, 8.5, 7.3 Hz 1H; H-5'), 2.78 (ddd, J=14.6, 8.3, 5.4 Hz 1H; H-4),2.51 (ddd, J=14.6, 8.5, 7.3 Hz 1H; H4'), 2.16 (s, 3H; Ac—$CH_3$), 1.40 (d, J=6.3 Hz, 3H; $CH_3$); $^{13}$C NMR: δ (ppm), 169.12 (Ac—C=O), 117.05 (CN), 82.09 (C-5), 75.20 (C-3), 65.84 (C-2), 38.70 (C-4), 20.70 (Ac—$CH_3$), 13.32 ($CH_3$).

EXAMPLE 6

Reaction of rac-2-methyltetrahydrothiophen-3-one

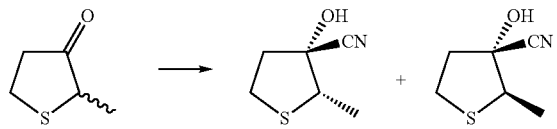

0.232 (2 mmol) of 2-methyltetrahydrothiophen-3-one were dissolved in 3 mL of t-butyl methyl ether and cooled to 0° C.

1 mL of (S)-HNL from *Hevea brasiliensis* having an activity of 5100 IU/mL were diluted with 2 mL of distilled water and adjusted to pH 4.40 with 10% citric acid. This aqueous enzymatic solution was added to the organic solution and stirred for 15 minutes at 0° C. to form an emusion. 0.3 mL (8.8 mmol) of HCN were then added to the reaction solution. After stirring for 60 minutes at 0° C., 3 mL of t-butyl methyl ether were added to the reaction and bound with 0.5 g Celite® 545 water and enzyme. The mixture was then dried over $Na_2SO_4$, filtered and freed from solvent.

Yield: (90% conversion) yellow oil of 3-cyano-2-methyltetrahydrothiophen-3-ol

For analytical purposes, the cyanohydrin was converted into the corresponding acetate and characterized as such.

(+)-cis Isomer: 10% de; $^1$H NMR: δ (ppm) 3.65 (qu, J=6.9 Hz, 1H; H-2), 3.12–2.70 (m, 3H; H-4, H-5, H-5'), 2.58-2.37 (m, 1H; H-4'), 2.10 (s, 3H; Ac—$CH_3$) 1.47 (d, J=6.9 Hz, 3H; $CH_3$); $^{13}$C NMR: δ (ppm), 169.02 (Ac—C=O), 115.54 (CN), 81.38 (C-3),48.06 (C-2), 38.70 (C-4), 26.95 (C-5), 20.98 (Ac—$CH_3$), 19.48 ($CH_3$).

(+)-trans Isomer: 10% de; $^1$H NMR: δ (ppm) 3.85 (qu, J=6.9 Hz, 1H; H-2), 3.12-2.70 (m, 3H; H-4, H-5, H-5'), 2.58–2.37 (m, 1H; H-4'), 2.14 (s, 3H; Ac—$CH_3$) 1.34 (d, J=6.9 Hz, 3H; $CH_3$); $^{13}$C NMR: δ (ppm), 168.97 (Ac—C=O), 117.00 (CN), 78.48 (C-3),48.74 (C-2), 38.66 (C-4), 26.34 (C-5), 20.88 (Ac—$CH_3$), 15.62 ($CH_3$).

EXAMPLE 7

Conversion of rac-5-methyltetrahydrothiophen-3-one

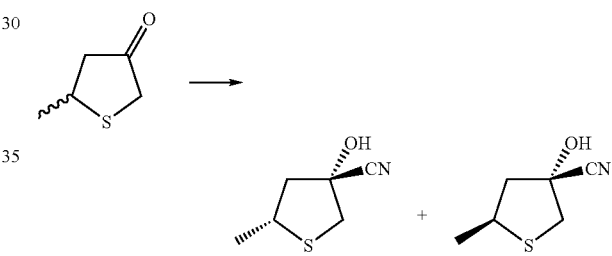

0.232 (2 mmol) of 2-methyltetrahydrothiophen-3-one were dissolved in 3 mL of t-butyl methyl ether and cooled to 0° C.

3 mL of (R)-HNL from *Prunus amygdalus* having an activity of 250 IU/mL were adjusted to pH 4.30 with 10% citric acid. This aqueous enzymatic solution was added to the organic solution and stirred for 15 minutes at 0° C. to form an emulsion. 0.3 mL (8.8 mmol) of HCN were then added to the reaction solution. After stirring for 60 minutes at 0° C., 3 mL of t-butyl methyl ether were added to the reaction and bound with 0.5 g of Celite® 545 water and enzyme. The mixture was then dried over $Na_2SO_4$, filtered and freed from solvent.

Yield: (95% conversion) yellow oil of 3-cyano-5-methyltetrahydrothiophen-3-ol

For analytical purposes, the cyanohydrin was converted into the corresponding acetate and characterized as such.

(−)-cis Isomer: 86% de; $^1$H NMR: δ (ppm) 3.77–33.6 (m, 3H; H-5, H-2, H-2'), 2.81 (dd, J=13.2, 6.6 Hz, 1H; H-4), 2.11 (m, 1H; H-4') 2.13 (s, 3H; Ac—$CH_3$), 1.41 (d, J=6.8 Hz, 3H; $CH_3$); $^{13}$C NMR: δ (ppm), 168.97 (Ac—C=O), 117.02 (CN), 76.67 (C-3), 49.35 (C-2), 41.24 (C-4), 38.51 (C-5), 22.00 (Ac—$CH_3$), 20.63 ($CH_3$).

(−)-trans Isomer: 95% de; $^1$H NMR: δ (ppm) 3.70 (m, 1H; H-5), 3.62 (d, J=11.9 Hz, 1H; H-2), 3.28 (d, J=11.9 Hz, 1H; H-2'), 2.88 (dd, J=13.2, 6.6 Hz, 1H; H-4), 2.12 (dd, J=13.2 Hz, 1H; H-4') 2.13 (s, 3H; Ac—$CH_3$), 1.40 (d, J=6.8 Hz, 3H;

CH$_3$); $^{13}$C NMR: δ (ppm), 168.99 (Ac—C=O), 117.47 (CN), 77.41 (C-3), 48.47 (C-2), 40.54 (C-4), 38.51 (C-5), 21.99 (Ac—CH$_3$), 20.89 (CH$_3$).

What is claimed is:

1. A process for preparing enantiomer-enriched heterocyclic (R)- and (S)-cyanohydrins of the formula (I),

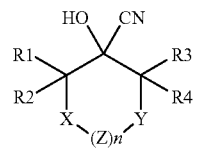

where R1, R2, R3, R4 independently of one another are H, an unbranched, branched or cyclic $C_1$–$C_{24}$, alkyl, alkenyl or alkynyl radical which can be unsubstituted, mono substituted or polysubstituted by substituents inert under the reaction conditions, where one or more carbon atoms in the chain can be replaced by an oxygen atom, a nitrogen atom, a sulfur atom, an SO or an SO$_2$ group, an aryl or heteroaryl or heterocyclic radical which can be unsubstituted, monosubstituted or polysubstituted by substituents inert under the reaction conditions, or halogen, hydroxyl, NR5R6, acetyl, oxo, $C_1$–$C_6$-carbalkoxy, $C_1$–$C_6$-carbalkoxyamino, COOR7, cyano, amide, benzoylamino or NO$_2$, R5 and R6 independently of one another can be H, unbranched, branched or cyclic $C_1$–$C_6$-alkyl radical, phenyl radical, benzyl radical, COOR7, or together form a $C_2$–$C_8$-alkylene or -heteroalkylene radical, R7 is H or $C_1$–$C_6$-alkyl, X and Y independently of one another can be a carbon atom which can be unsubstituted, monosubstituted or disubstituted by substituents inert under the reaction conditions, or a radical selected from the group consisting of N, O, S, or NR5R6, where R5 and R6 are as defined above, SO or SO$_2$, n is 0, 1, 2 or 3, Z is a carbon atom which can be unsubstituted, monosubstituted or disubstituted by substituents inert under the reaction conditions, or a radical selected from the group consisting of N, O, S, or NR5R6, where R5 and R6 are as defined above, SO or SO$_2$, and at least one of the radicals X, Y and Z is not a carbon atom, where the compounds of the formula (I), depending on the ring size, can have one or more double bonds in the ring, with the proviso that in the 5-membered ring the double bond is not conjugated with the —C(OH)CN-group, and/or can be monoanellated or polyanellated by 5-membered, 6-membered or 7-membered rings containing 0 to 3 heteroatoms, and/or can be bridged by an unbranched or branched $C_1$–$C_6$-alkylene radical, the alkyl chain of which can be interrupted by one or more heteroatoms and/or can have a double bond, which comprises reacting ketones of the formula (II),

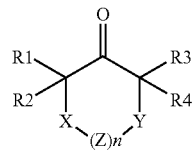

where R1, R2, R3, R4, X, Y, Z and n have the meanings given above, using a non-immobilized (R)- or (S)-hydroxynitrile lyase in the organic, aqueous or two-phase system or in emulsion in the presence of a cyanide-group donor to give the desired (R)- and (S)-cyanohydrins.

2. The process as claimed in claim 1, wherein ketones of the formula (II) are used as starting materials, where R1, R2, R3 and R4 independently of one another are H, a saturated or monounsaturated, unbranched, branched or cyclic $C_1$–$C_{12}$-alkyl radical in which a carbon atom in the chain can be replaced by an oxygen atom, a nitrogen atom or a sulfur atom, a phenyl, biphenyl or naphthyl radical, where the radicals can be substituted by one or more substituents selected from the group consisting of $C_1$–$C_6$-alkyl, $C_1$–$C_6$-alkoxy, $C_1$–$C_{12}$-alkylalkoxy, $C_1$–$C_{20}$-aryloxy, halogen, hydroxyl, oxo, carboxyl, phenyl which can be unsubstituted or monosubstituted or disubstituted by halogen, hydroxyl, $C_1$–C4-alkyl or $C_1$–$C_4$-alkoxy, or halogen, hydroxyl, oxo, $C_1$–$C_6$-carbalkoxy, $C_1$–$C_6$-carbalkoxyamino, NR5R6, acetyl, COOR7, cyano, amide, benzoylamino or NO$_2$, R5 and R6 independently of one another can be H or an unbranched, cyclic or branched $C_1$–$C_6$-alkyl radical or together form a $C_2$–$C_8$-alkylene radical, R7 is H or $C_1$–$C_6$-alkyl, n is 0, 1 or 2, X, Y and Z independently of one another are a carbon atom which can be unsubstituted or monosubstituted or disubstituted by $C_1$–$C_6$-alkyl, $C_1$–$C_6$-alkoxy, $C_1$–$C_{12}$-alkylalkoxy, $C_1$–$C_{20}$-aryloxy halogen, hydroxyl, oxo, carboxyl, phenyl which can be unsubstituted or monosubstituted or disubstituted by halogen, hydroxyl, $C_1$–$C_4$-alkyl or $C_1$–$C_4$-alkoxy, or a radical selected from the group consisting of N, O, S or NR5R6, where one or two of the radicals X, Y or Z is not a carbon atom, where the ketones of the formula (II) when n=0 do not contain a double bond, when n=1 do not contain a double bond, or contain one double bond and when n=2 contain zero to two double bonds and/or can be anellated by a 5-membered or 6-membered ring containing 0 to 1 heteroatoms, and/or can be be bridged by an unbranched or branched $C_1$–$C_6$-alkylene radical which can have a double bond.

3. The process as claimed in claim 1, wherein the organic diluents used for the reaction in the organic system are water-immiscible or slightly water-miscible aliphatic or aromatic hydrocarbons which may be halogenated, alcohols, ethers or esters or mixtures.

4. The process as claimed in claim 1, wherein the reaction is performed in emulsion.

5. The process as claimed in claim 1, wherein the enantioselective reaction is carried out in an aqueous system, where a solution or acetate buffer, borate butter, phthalate buffer, citrate buffer or phosphate buffer solution containing the corresponding hydroxynitrile lyase or mixtures of these buffer solutions serves as reaction medium.

6. The process as claimed in claim 1, wherein the hydroxynitrile lyase used is a native or recombinant (R)- or (S)-hydroxynitrile lyase.

7. The process as claimed in claim 6, where the hydroxynitrile lyase used is a native (S)-hydroxynitrile lyase from manioc or *Hevea brasiliensis*, recombinant (S)-hydroxynitrile lyase from genetically modified microorganisms selected from the group consisting of *Pichia pastoris, E. coli* or *Saccharomyces cerevisiae*, native (R)-hydroxynitrile lyases from *Prunus amygdalus, Prunus laurocerasus* or *Prunus serotina*, or recombinant (R)-hydroxynitrile lyases.

8. The process as claimed in claim 1, wherein the cyanide group donor is prussic acid, alkali metal cyanide or cyanohydrins of the general formula (III),

R7R8C(OH)(CN)

where R7 and R8 independently of one another are hydrogen or an unsubstituted hydrocarbon group, or R7 and R8 together form an alkylene group having 4 or 5 carbon atoms, where R7 and R8 are not simultaneously hydrogen.

* * * * *